United States Patent
Blank et al.

(10) Patent No.: US 8,504,128 B2
(45) Date of Patent: Aug. 6, 2013

(54) METHOD AND APPARATUS FOR COUPLING A CHANNELED SAMPLE PROBE TO TISSUE

(75) Inventors: Thomas B. Blank, Gilbert, AZ (US);
Stephen L. Monfre, Gilbert, AZ (US);
Kevin H. Hazen, Gilbert, AZ (US);
Timothy L. Ruchti, Gurnee, IL (US);
Christopher Slawinski, Mesa, AZ (US);
Sedar R. Brown, Phoenix, AZ (US)

(73) Assignee: GLT Acquisition Corp., Irvine, CA (US)

( * ) Notice: Subject to any disclaimer, the term of this patent is extended or adjusted under 35 U.S.C. 154(b) by 1456 days.

(21) Appl. No.: 12/109,224

(22) Filed: Apr. 24, 2008

(65) Prior Publication Data
US 2008/0319382 A1 Dec. 25, 2008

Related U.S. Application Data

(63) Continuation-in-part of application No. 11/031,103, filed on Jan. 6, 2005, now abandoned, and a continuation-in-part of application No. 11/335,773, filed on Jan. 18, 2006, now abandoned, which is a continuation of application No. 10/472,856, filed as application No. PCT/US03/07065 on Mar. 7, 2003, now Pat. No. 7,133,710.

(60) Provisional application No. 60/536,197, filed on Jan. 12, 2004, provisional application No. 60/534,834, filed on Jan. 6, 2004, provisional application No. 60/566,568, filed on Apr. 28, 2004, provisional application No. 60/362,885, filed on Mar. 8, 2002, provisional application No. 60/362,899, filed on Mar. 8, 2002, provisional application No. 60/448,840, filed on Feb. 19, 2003, provisional application No. 60/916,759, filed on May 8, 2007, provisional application No. 60/955,197, filed on Aug. 10, 2007, provisional application No. 60/938,660, filed on May 17, 2007, provisional application No. 61/032,859, filed on Feb. 29, 2008.

(51) Int. Cl.
*A61B 5/1455* (2006.01)

(52) U.S. Cl.
USPC ............ 600/310; 600/316; 600/322; 600/344

(58) Field of Classification Search
USPC ................. 600/310, 316, 322, 323, 326, 333, 600/335, 336, 340, 344, 473, 476; 401/175, 401/263, 266
See application file for complete search history.

(56) References Cited

U.S. PATENT DOCUMENTS

| | | | |
|---|---|---|---|
| 4,033,054 A | 7/1977 | Fukuoka | |
| 4,213,462 A | 7/1980 | Sato | |

(Continued)

FOREIGN PATENT DOCUMENTS

| | | |
|---|---|---|
| CN | 1214768 | 4/1999 |
| DE | 2640987 | 3/1978 |

(Continued)

OTHER PUBLICATIONS

Webster's II New Riverside University Dictionary: The Riverside Publishing Company, 1994, p. 1000.

(Continued)

*Primary Examiner* — Eric Winakur
*Assistant Examiner* — Chu Chuan (JJ) LIU
(74) *Attorney, Agent, or Firm* — Knobbe, Martens, Olson & Bear LLP

(57) ABSTRACT

Sampling is controlled in order to enhance analyte concentration estimation derived from noninvasive sampling. More particularly, sampling is controlled using controlled fluid delivery to a region between a tip of a sample probe and a tissue measurement site. The controlled fluid delivery enhances coverage of a skin sample site with the thin layer of fluid. Delivery of contact fluid is controlled in terms of spatial delivery, volume, thickness, distribution, temperature, and/or pressure.

27 Claims, 6 Drawing Sheets

U.S. PATENT DOCUMENTS

| | | | | |
|---|---|---|---|---|
| 4,291,293 | A * | 9/1981 | Yamada et al. | 338/4 |
| 4,321,930 | A | 3/1982 | Jobsis | |
| 4,548,505 | A | 10/1985 | Ono | |
| 4,674,338 | A | 6/1987 | Carpenter | |
| 4,755,413 | A * | 7/1988 | Morris | 428/138 |
| 4,798,955 | A | 1/1989 | Rosenthal | |
| 4,866,644 | A | 9/1989 | Shenk et al. | |
| 4,882,492 | A | 11/1989 | Schlager | |
| 5,007,423 | A | 4/1991 | Branstetter et al. | |
| 5,039,492 | A * | 8/1991 | Saaski et al. | 422/82.09 |
| 5,068,536 | A | 11/1991 | Rosenthal | |
| 5,070,874 | A | 12/1991 | Barnes et al. | |
| 5,131,391 | A | 7/1992 | Sakai et al. | |
| 5,170,786 | A | 12/1992 | Thomas | |
| 5,285,783 | A | 2/1994 | Secker | |
| 5,299,570 | A | 4/1994 | Hatschek | |
| 5,348,003 | A | 9/1994 | Caro | |
| 5,361,758 | A | 11/1994 | Hall et al. | |
| 5,398,681 | A | 3/1995 | Kupershmidt | |
| 5,448,662 | A | 9/1995 | Kittell | |
| 5,492,118 | A | 2/1996 | Gratton | |
| 5,506,482 | A | 4/1996 | Teramatsu | |
| 5,507,288 | A | 4/1996 | Bocker et al. | |
| 5,517,301 | A * | 5/1996 | Dave | 356/237.1 |
| 5,548,674 | A | 8/1996 | Rondeau | |
| 5,596,987 | A | 1/1997 | Chance | |
| 5,619,195 | A | 4/1997 | Allen | |
| 5,632,273 | A | 5/1997 | Suzuki | |
| 5,636,634 | A | 6/1997 | Kordis | |
| 5,655,530 | A | 8/1997 | Messerschmidt | |
| 5,661,843 | A | 8/1997 | Rickenbach | |
| 5,671,317 | A | 9/1997 | Weishaupt | |
| 5,687,717 | A | 11/1997 | Halpern et al. | |
| 5,725,480 | A | 3/1998 | Oosta | |
| 5,730,140 | A | 3/1998 | Fitch | |
| 5,747,806 | A | 5/1998 | Khalil et al. | |
| 5,750,994 | A | 5/1998 | Schlager | |
| 5,769,076 | A | 6/1998 | Maekawa | |
| 5,770,454 | A | 6/1998 | Essenpreis et al. | |
| 5,772,347 | A * | 6/1998 | Gueret | 401/263 |
| 5,823,951 | A | 10/1998 | Messerschmidt | |
| 5,825,488 | A | 10/1998 | Kohl et al. | |
| 5,830,132 | A | 11/1998 | Robinson | |
| 5,869,075 | A | 2/1999 | Krzysik | |
| 5,877,664 | A | 3/1999 | Jackson, Jr. | |
| 5,879,373 | A | 3/1999 | Roper et al. | |
| 5,891,021 | A | 4/1999 | Dillon | |
| 5,912,656 | A | 6/1999 | Tham et al. | |
| 5,935,062 | A | 8/1999 | Messerschmidt et al. | |
| 5,945,676 | A | 8/1999 | Khalil et al. | |
| 5,956,150 | A | 9/1999 | Kanne | |
| 5,978,691 | A | 11/1999 | Mills | |
| 6,014,756 | A | 1/2000 | Dottling | |
| 6,040,578 | A | 3/2000 | Malin et al. | |
| 6,045,511 | A | 4/2000 | Ott | |
| 6,067,463 | A | 5/2000 | Jeng et al. | |
| 6,088,605 | A | 7/2000 | Griffith et al. | |
| 6,093,156 | A | 7/2000 | Cunningham et al. | |
| 6,095,974 | A | 8/2000 | Shemwell et al. | |
| 6,115,673 | A | 9/2000 | Malin et al. | |
| 6,119,031 | A * | 9/2000 | Crowley | 600/310 |
| 6,144,868 | A | 11/2000 | Parker | |
| 6,152,876 | A | 11/2000 | Robinson | |
| 6,157,041 | A | 12/2000 | Thomas et al. | |
| 6,167,290 | A * | 12/2000 | Yang et al. | 600/322 |
| 6,178,564 | B1 * | 1/2001 | Leonard et al. | 4/223 |
| 6,180,416 | B1 | 1/2001 | Kuenik et al. | |
| 6,230,034 | B1 | 5/2001 | Messerschmidt | |
| 6,233,471 | B1 | 5/2001 | Berner et al. | |
| 6,236,047 | B1 | 5/2001 | Malin et al. | |
| 6,240,306 | B1 | 5/2001 | Rohrscheib et al. | |
| 6,272,364 | B1 | 8/2001 | Kurnik | |
| 6,280,381 | B1 | 8/2001 | Malin et al. | |
| 6,289,230 | B1 | 9/2001 | Chaiken et al. | |
| 6,304,766 | B1 | 10/2001 | Colvin, Jr. | |
| 6,326,160 | B1 | 12/2001 | Dunn et al. | |
| 6,330,464 | B1 | 12/2001 | Colvin, Jr. et al. | |
| 6,334,360 | B1 | 1/2002 | Chen | |
| 6,381,489 | B1 | 4/2002 | Ashibe | |
| 6,400,974 | B1 | 6/2002 | Lesho | |
| 6,405,065 | B1 | 6/2002 | Malin et al. | |
| 6,411,373 | B1 | 6/2002 | Garside et al. | |
| 6,411,838 | B1 | 6/2002 | Nordstrom et al. | |
| 6,415,167 | B1 | 7/2002 | Blank et al. | |
| 6,421,549 | B1 | 7/2002 | Jacques | |
| 6,441,388 | B1 | 8/2002 | Thomas | |
| 6,442,408 | B1 | 8/2002 | Wenzel et al. | |
| 6,449,500 | B1 | 9/2002 | Asai et al. | |
| 6,456,870 | B1 | 9/2002 | Rennert et al. | |
| 6,475,800 | B1 | 11/2002 | Hazen et al. | |
| 6,487,429 | B2 | 11/2002 | Hockersmith et al. | |
| 6,493,566 | B1 | 12/2002 | Ruchti et al. | |
| 6,501,982 | B1 | 12/2002 | Ruchti et al. | |
| 6,507,687 | B1 | 1/2003 | Juskaitis et al. | |
| 6,512,937 | B2 | 1/2003 | Blank et al. | |
| 6,512,982 | B2 | 1/2003 | Yang et al. | |
| 6,526,300 | B1 * | 2/2003 | Kiani et al. | 600/322 |
| 6,528,809 | B1 | 3/2003 | Thomas | |
| 6,546,269 | B1 | 4/2003 | Kurnik | |
| 6,585,370 | B2 | 7/2003 | Zelman | |
| 6,631,282 | B2 | 10/2003 | Rule et al. | |
| 6,641,533 | B2 | 11/2003 | Causey, III et al. | |
| 6,690,958 | B1 | 2/2004 | Walker et al. | |
| 6,788,965 | B2 | 9/2004 | Ruchti | |
| 6,839,583 | B1 | 1/2005 | Lewandowski et al. | |
| 6,927,843 | B2 | 8/2005 | Dick | |
| 7,133,710 | B2 | 11/2006 | Acosta et al. | |
| 2002/0026106 | A1 | 2/2002 | Khalil et al. | |
| 2003/0040663 | A1 | 2/2003 | Rule | |
| 2003/0216627 | A1 | 11/2003 | Lorenz | |
| 2003/0216630 | A1 | 11/2003 | Jersey-Willuhn et al. | |
| 2004/0068163 | A1 | 4/2004 | Ruchti | |
| 2004/0077937 | A1 | 4/2004 | Yarden | |
| 2004/0127777 | A1 | 7/2004 | Ruchti | |
| 2004/0163032 | A1 | 8/2004 | Guo | |
| 2004/0267105 | A1 * | 12/2004 | Monfre et al. | 600/344 |
| 2005/0007125 | A1 | 1/2005 | Heger | |
| 2005/0267342 | A1 | 12/2005 | Blank et al. | |
| 2006/0200017 | A1 | 9/2006 | Monfre et al. | |

FOREIGN PATENT DOCUMENTS

| | | |
|---|---|---|
| EP | 1254631 | 11/2002 |
| JP | 04/215742 | 8/1992 |
| JP | 08-215180 | 8/1996 |
| JP | 2001-037741 | 2/2001 |
| JP | 2001-299727 | 10/2001 |
| JP | 2002535023 | 10/2002 |
| WO | WO 96/28084 | 9/1996 |
| WO | WO 97/05819 | 2/1997 |
| WO | WO 97/28437 | 8/1997 |
| WO | WO 00/22982 | 4/2000 |
| WO | WO 00/42907 | 7/2000 |
| WO | WO 00/76575 A3 | 12/2000 |
| WO | WO 01/31304 | 5/2001 |
| WO | WO 01/58355 | 8/2001 |

OTHER PUBLICATIONS

Diabetes Statistics. Bethesda, MD: National Institute of Health, Publication No. 98-3926, Nov. 1997.

The Diabetes Control and Complications Trial Research Group. "The effect of intensive treatment of diabetes on the development and progression of long-term complications in insulin-dependent diabetes mellitus." N Eng J of Med 1993;329:977-86.

U.K. Prospective Diabetes Study (UKPDS) Group, "Intensive blood-glucose control with sulphonylureas or insulin compared with conventional treatment and risk of complications in patients with type 2 diabetes," *Lancet*, vol. 352, pp. 837-853, 1998.

Ohkubo, Y., H. Kishikawa, E. Araki, T. Miyata, S. Isami, S. Motoyoshi, Y. Kojima, N. Furuyoshi, and M. Shichizi, "Intensive insulin therapy prevents the progression of diabetic microvascular complications in Japanese patients with non-insulin-dependent diabetes mellitus: a randomized prospective 6-year study," *Diabetes Res Clin Pract*, vol. 28, pp. 103-117, 1995.

Savitzky, A. and M. J. E. Golay. "Smoothing and Differentiation of Data by Simplified Least Squares Procedures," *Anal. Chem.*, vol. 36, No. 8, pp. 1627-1639, 1964.

Hazen, Kevin H. "Glucose Determination in Biological Matrices Using Near-Infrared Spectr Sage, Burton H. "FDA Panel Approves Cygnus's Noninvasive GlucoWatch™", *Diabetes Technology & Therapeutics*, 2, 2000, 115-116.oscopy", doctoral dissertation, University of Iowa, 1995.

Tamada, J.A., S. Garg, L. Jovanovic, K.R. Pitzer, S. Fermi, R.O. Potts, "Noninvasive Glucose Monitoring Comprehensive Clinical Results," *JAMA*, vol. 282, No. 19, pp. 1839-1844, Nov. 17, 1999.

"GlucoWatch Automatic Glucose Biographer and AutoSensors", Cygnus Inc., Document #1992-00, Rev. Mar. 2001.

Trajanowski, Zlatko; Brunner, Gernot A.; Schaupp, Lucas; Ellmerer, Martin; Wach, Paul; Pieber, Thomas R,; Kotanko, Peter; Skrabai, Falko "Open-Flow Microperfusion of Subcutaneous Adipose Tissue for ON-Line Continuous Ex Vivo Measurement of Glucose Concentration", *Diabetes Care*, 20, 1997, 1114-1120.

Trajanowski, Zlatko; Wach, Paul; Gfrerer, Robert "Portable Device for Continuous Fractionated Blood Sampling and Continuous ex vivo Blood Glucose Monitoring", *Biosensors and Bioelectronics*, 11, 1996, 479-487.

Gross, Todd M.; Bode, Bruce W.; Einhorn, Daniel; Kayne, David M.; Reed, John H.; White, Neil H.; Mastrototaro, John J. "Performance Evaluation of the MiniMed Continuous Glucose Monitoring System During Patient Home Use", *Diabetes Technology & Therapeutics*, 2, 2000, 49-56.

Rebrin, Kerstin; Steil, Gary M.; Antwerp, William P. Van; Mastrototaro, John J. "Subcutaneous Glucose Predicts Plasma Glucose Independent of Insulin: Implications for Continuous Monitoring", *Am., J. Physiol.*, 277, 1999, E561-E571, 0193-1849/99, The American Physiological Society, 1999.

Geladi, P., D. McDougall and H. Martens. "Linearization and Scatter-Correction for Near-Infrared Reflectance Spectra of Meat," *Applied Spectroscopy*, vol. 39, pp. 491-500, 1985.

R.J. Barnes, M.S. Dhanoa, and S. Lister, Standard Normal Variate Transformation and De-trending of Near-Infrared Diffuse Reflectance Spectra, *Applied Spectroscopy*, 43, pp. 772-777, 1989.

T. Isaksson and B. R. Kowalski, "Piece-Wise Multiplicative Scatter Correction Applied to Near-Infrared Diffuse Transmittance Data From Meat Products", *Applied Spectroscopy*, 47, pp. 702-709, 1993.

H. Martens and E. Stark, "Extended multiplicative signal correction and spectral interference subtraction: new preprocessing methods for near infrared spectroscopy", *J. Pharm Biomed Anal*, 9, pp. 625-635, 1991.

T. Isaksson, Z. Wang, and B. R. Kowalski, Optimised scaling (OS-2) regression applied to near infrared . . . food products, *J. Near Infrared Spectroscopy*, 1, pp. 85-97, 1993.

Sum, S.T., "Spectral Signal Correction for Multivariate Calibration," Doctoral Disseration, University of Delaware, Summer 1998.

Sum, S.T. and S.D. Brown, "Standardization of Fiber-Optic Probes for Near-Infrared Multivariate Calibrations," *Applied Spectroscopy*, vol. 52, No. 6, pp. 869-877, 1998.

T. B. Blank, S.T. Sum, S.D. Brown and S.L. Monfre, "Transfer of near-infrared multivariate calibrations without standards," *Analytical Chemistry*, 68, pp. 2987-2995, 1996.

Massart, et al.; *Data Handling in Scinece and Technology*—vol. 2; Chemometrics: a textbook; 1988 Elsevier Science Publishing Co., Inc. pp. 215-253.

Oppenheim, Alan V. and R. W. Schafer, *Digital Signal Processing*, Englewood Cliffs, NJ: Prentice Hall, 1975, pp. 195-271.

Otto, M., Statistics and Computer Application in Analytical Chemistry; *Chemometrics*, Weinheim: Wiley-VCH, 1999.

Beebe, K.R., R.J. Pell and M.B. Seasholtz, *Chemometrics A Practical Guide*, New York: John Wiley & Sons, Inc., 1998.

M.A. Sharaf, D.L. Illman and B.R. Kowalski, *Chemometrics*, New York: John Wiley & Sons, Inc., 1996.

* cited by examiner

METHOD AND APPARATUS FOR COUPLING A CHANNELED SAMPLE PROBE TO TISSUE

CROSS REFERENCES TO RELATED APPLICATIONS

This application:
is a continuation-in-part of U.S. patent application Ser. No. 11/031,103, filed Jan. 6, 2005, which claims priority from U.S. provisional patent application Ser. No. 60/536,197, filed Jan. 12, 2004; U.S. provisional patent application Ser. No. 60/534,834, filed Jan. 6, 2004; and U.S. provisional patent application Ser. No. 60/566,568, filed Apr. 28, 2004;
is a continuation-in-part of U.S. patent application No. 11/335,773, filed Jan. 18, 2006, which is a continuation of U.S. patent application Ser. No. 10/472,856, filed Sep. 18, 2003, which is a 371 national stage application of PCT application no. PCT/US03/07065, filed Mar. 7, 2003, which claims benefit of U.S. provisional patent application Ser. No. 60/362,885, filed Mar. 8, 2002, U.S. provisional patent application Ser. No. 60/362,899, filed Mar. 8, 2002, and U.S. provisional patent application Ser. No. 60/448,840, filed Feb. 19, 2003; and
claims benefit of:
U.S. provisional patent application No. 60/916,759 filed May. 8, 2007;
U.S. provisional patent application No. 60/955,197 filed Aug. 10, 2007;
U.S. provisional patent application No. 60/938,660 filed May. 17, 2007; and
U.S. provisional patent application No. 61/032,859 filed Feb. 29, 2008;
all of which are incorporated herein in their entirety by this reference thereto.

BACKGROUND OF THE INVENTION

1. Field of the Invention

This invention relates generally to noninvasive measurement of biological parameters using spectroscopy. More particularly, a method and apparatus are disclosed for fluid delivery between an analyzer and a tissue sample to aid in parameter stability during optical sampling.

2. Discussion of the Prior Art

Technical Background

In-vivo measurement of a tissue property or an analyte concentration using optical based analyzers requires that a tissue measurement region be positioned and coupled with respect to an optical interface or probe, such as a tip of a sampling module or tip of a sample probe. The requirements of a sampling interface system for probe placement and coupling depends upon the nature of the tissue properties and analytes under consideration, the optical technology being applied, and the variability of the tissue sample site. Demanding in-vivo applications require a high degree of sampling reproducibility. In one example, a relatively unskilled operator or user must perform the optical measurement. One exemplary application is the noninvasive estimation of glucose concentration through near-infrared spectroscopy in a variety of environments. This problem is further considered through a discussion of the target application and the structure, variability, and dynamic properties of live tissue.

Diabetes

Diabetes is a chronic disease that results in abnormal production and use of insulin, a hormone that facilitates glucose uptake into cells. Diabetics have increased risk in three broad categories: cardiovascular heart disease, retinopathy, and neuropathy. The estimated total cost to the United States economy alone exceeds $90 billion per year. *Diabetes Statistics*, National Institutes of Health, Publication No. 98-3926, Bethesda, Md. (November 1997). Long-term clinical studies show that the onset of diabetes related complications are significantly reduced through proper control of blood glucose concentrations [The Diabetes Control and Complications Trial Research Group, *The effect of intensive treatment of diabetes on the development and progression of long-term complications in insulin-dependent diabetes mellitus*, N Eng J of Med 1993; 329:977-86. A vital element of diabetes management is the self-monitoring of blood glucose concentration by diabetics in the home environment. However, current monitoring techniques discourage regular use due to the inconvenient and painful nature of drawing blood through the skin prior to analysis.

Noninvasive Glucose Concentration Estimation

There exist a number of noninvasive approaches for glucose concentration estimation. These approaches vary widely, but have at least two common steps. First, an apparatus is used to acquire a reading from the body without obtaining a biological sample for every glucose concentration estimation. Second, an algorithm is used to convert the noninvasive reading into a glucose concentration estimation or determination.

Technologies

A number of previously reported technologies for estimating glucose concentration noninvasively exist that involve the measurement of a tissue related variable. One species of noninvasive glucose concentration analyzer uses spectroscopy to acquire a signal or spectrum from the body. Examples include far-infrared absorbance spectroscopy, tissue impedance, Raman, and fluorescence, as well as techniques using light from the ultraviolet through the infrared [ultraviolet (200 to 400 nm), visible (400 to 700 nm), near-infrared (700 to 2500 nm or 14,286 to 4000 $cm^{-1}$), and mid-infrared (2500 to 14,285 nm or 4000 to 700 $cm^{-1}$)]. Notably, noninvasive techniques do not have to be based upon spectroscopy. For example, a bioimpedance meter is a noninvasive device. In this document, any device that reads glucose concentration from the body without penetrating the skin or collecting a biological sample with each sample is referred to as a noninvasive glucose concentration analyzer. For the purposes of this document, X-rays and magnetic resonance imagers (MRI's) are not considered to be defined in the realm of noninvasive technologies. It is noted that noninvasive techniques are distinct from invasive techniques in that the sample analyzed is a portion of the human body in-situ, not a biological sample acquired from the human body. The actual tissue volume that is sampled is the portion of irradiated tissue from which light is diffusely reflected, transflected, or diffusely transmitted to the spectrometer detection system.

Instrumentation

A number of spectrometer configurations are reported for collecting noninvasive spectra of regions of the body. Typically a spectrometer has one or more beam paths from a source to a detector. Optional light sources include a blackbody source, a tungsten-halogen source, one or more light emitting diodes, or one or more laser diodes. For multi-wavelength spectrometers a wavelength selection device is optionally used or a series of optical filters are optionally used for wavelength selection. Wavelength selection devices include dispersive elements, such as one or more plane, concave, ruled, or holographic grating.

Sampling

Light is directed to and from a glucose concentration analyzer to a tissue sample site by optical methods, such as through a light pipe, fiber-optics, a lens system, free space optics, and/or a light directing mirror system. Typically, one or more of three modes are used to collect noninvasive scans: transmittance, transflectance, and/or diffuse reflectance. Collected signal is converted to a voltage and sampled through an analog-to-digital converter for analysis on a microprocessor based system and the result displayed.

Human Tissue/Light Interaction

When incident light is directed onto the skin surface, a part of it is reflected while the remaining part penetrates the skin surface. The proportion of reflected light energy is strongly dependent on the angle of incidence. At nearly perpendicular incidence, about four percent of the incident beam is reflected due to the change in refractive index between air ($\eta_D=1.0$) and dry stratum corneum ($\eta_D=1.55$). For normally incident radiation, this specular reflectance component is as high as seven percent, because the very rigid and irregular surface of the stratum corneum produces off-normal angles of incidence. Regardless of skin color, specular reflectance of a nearly perpendicular beam from normal skin ranges between four and seven percent over the entire spectrum from 250 to 3000 nm. The air-stratum corneum border gives rise to a regular reflection. Results indicate that the indices of refraction of most soft tissue (skin, liver, heart, etc) lie within the 1.38-1.41 range with the exception of adipose tissue, which has a refractive index of approximately 1.46. The 93 to 96 percent of the incident beam that enters the skin is attenuated due to absorption and/or scattering within any of the layers of the skin. These two processes taken together essentially determine the penetration of light into skin, as well as remittance of scattered light from the skin.

Noninvasive Glucose Concentration Determination

There are a number of reports of noninvasive glucose technologies. Some of these relate to general instrumentation configurations required for noninvasive glucose concentration estimation while others refer to sampling technologies. Those related to the present invention are briefly reviewed, infra.

Specular Reflectance

R. Messerschmidt, D. Sting, Blocker device for eliminating specular reflectance from a diffuse reflectance spectrum, U.S. Pat. No. 4,661,706 (Apr. 28, 1987) describe a reduction of specular reflectance by a mechanical device. A blade-like device "skims" the specular light before it impinges on the detector. This system leaves alignment concerns and improvement in efficiency of collecting diffusely reflected light is needed.

R. Messerschmidt, M. Robinson, Diffuse reflectance monitoring apparatus, U.S. Pat. No. 5,636,633 (Jun. 10, 1997) describe a specular control device for diffuse reflectance spectroscopy using a group of reflecting and open sections.

R. Messerschmidt, M. Robinson, Diffuse reflectance monitoring apparatus, U.S. Pat. No. 5,935,062 (Aug. 10, 1999) and R. Messerschmidt, M. Robinson, Diffuse reflectance monitoring apparatus, U.S. Pat. No. 6,230,034 (May 8, 2001) describe a diffuse reflectance control device that discriminates between diffusely reflected light that is reflected from selected depths. This control device additionally acts as a blocker to prevent specularly reflected light from reaching the detector.

S. Malin, G Khalil, Method and apparatus for multi-spectral analysis of organic blood analytes in noninvasive infrared spectroscopy, U.S. Pat. No. 6,040,578 (Mar. 21, 2000) describe the use of specularly-reflected light in regions of high water absorbance, such as 1450 and 1900 nm, to mark the presence of outlier spectra wherein the specularly reflected light is not sufficiently reduced.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe a mechanical device for applying sufficient and reproducible contact of the apparatus to the sample medium to minimize specular reflectance. Further, the apparatus allows for reproducible applied pressure to the sample site and reproducible temperature at the sample site.

Coupling Fluid

A number of sources describe coupling fluids as a consideration in noninvasive sampling methods and apparatus. Coupling fluids have been long known and understood in the field of optics. Some coupling fluids are used to fill optical irregularities. Others are used for refractive index matching. Some, such as glycerol when used in conjunction with near-infrared light, absorb in the wavelength region of interest. Several reports of optical coupling fluids and a report of a coupling fluid are described, infra.

R. Messerschmidt, Method for non-invasive blood analyte measurement with improved optical interface, U.S. Pat. No. 5,655,530, Aug. 12, 1997 and R. Messerschmidt, Method for non-invasive blood analyte measurement with improved optical interface, U.S. Pat. No. 5,823,951, (Oct. 20, 1998) describe an index-matching medium to improve the interface between a sensor probe and a skin surface during spectrographic analysis. These patents teach an optical coupling medium containing both perfluorocarbons and chlorofluorocarbons that have minimal absorbance in the near-infrared. Since they are known carcinogens, chlorofluorocarbons (CFC's) are unsuitable for use in preparations to be used on living tissue. Furthermore, use of CFC's poses a well-known environmental risk. Additionally, Messerschmidt's interface medium is formulated with substances that are likely to leave artifacts in spectroscopic measurements.

M. Robinson, R. Messerschmidt, Method for non-invasive blood analyte measurement with improved optical interface, U.S. Pat. No. 6,152,876 (Nov. 28, 2000) and M. Rohrscheib, C. Gardner, M. Robinson, Method and apparatus for non-invasive blood analyte measurement with fluid compartment equilibration, U.S. Pat. No. 6,240,306 (May 29, 2001) describe an index-matching optical coupling fluid used to improve the interface between the sensor probe and skin surface during spectroscopic analysis. The index-matching medium is preferably a composition containing chlorofluorocarbons in combination with optionally added perfluorocarbons.

T. Blank, G. Acosta, M. Mattu, S. Monfre, Fiber optic probe guide placement guide, U.S. Pat. No. 6,415,167 (Jul. 2, 2002) describe a coupling fluid of one or more fluorocarbons where a quantity of the coupling fluid is placed at an interface of the tip of an optical probe of a sample module and a measurement site. Advantageously, perfluoro compounds and fluorocarbons lack the toxicity associated with chlorofluorocarbons.

Pressure

E. Chan, B. Sorg, D. Protsenko, M. O'Neil, M. Motamedi, A. Welch, *Effects of compression on soft tissue optical properties*, IEEE Journal of Selected Topics in Quantum Electronics, Vol. 2, no. 4, 943-950 (1996) describe the effect of pressure on absorption and reduced scattering coefficients from 400 to 1800 nm. Most specimens show an increase in the scattering coefficient with compression.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe in a first embodiment a noninvasive glucose concentration estimation apparatus for either varying the pressure applied to a sample site or maintaining a constant pressure on a sample site in a controlled and reproducible manner by moving a sample probe along the z-axis perpendicular to the sample site surface. In an additional described embodiment, the arm sample site platform is moved along the z-axis that is perpendicular to the plane defined by the sample surface by raising or lowering the sample holder platform relative to the analyzer probe tip. The '012 patent further teaches proper contact between the probe tip and the sample site to be that point at which specularly-reflected light is substantially zero at the water bands at 1950 and 2500 nm.

M. Makarewicz, M. Mattu, T. Blank, G. Acosta, E. Handy, W. Hay, T. Stippick, B. Richie, Method and apparatus for minimizing spectral interference due to within and between sample variations during in-situ spectral sampling of tissue, U.S. patent application Ser. No. 09/954,856 (filed Sep. 17, 2001) describe a temperature and pressure controlled sample interface. The means of pressure control is a set of supports for the sample that control the natural position of the sample probe relative to the sample.

Data Processing

Several approaches exist that employ diverse preprocessing and post processing methods to remove spectral variation related to the sample and instrument variation: These include: normalization, smoothing, derivatives, multiplicative signal correction, piecewise multiplicative scatter correction, extended multiplicative signal correction, pathlength correction with chemical modeling and optimized scaling, and finite impulse response filtering. A goal of these techniques is to attenuate the noise and instrument variation while maximizing the signal of interest.

Problem

It is desirable to provide a means of assuring that the same tissue sample volume is repeatably sampled, thus minimizing sampling errors due to mechanical tissue distortion, specular reflectance, and probe placement. It would also be highly advantageous to provide a coupling medium to provide a constant interface between an optical probe and the skin at a tissue measurement site that is non-toxic and non-irritating and that doesn't introduce error into spectroscopic measurements. Still further, it would be advantageous to couple a sample probe to skin without inducing spectrally observed stress/strain features.

SUMMARY OF THE INVENTION

A fluid placed on the surface of tissue at a tissue measurement site, such as a coupling medium or alternatively an optical coupling fluid, is used to enhance performance of an optical analyzer coupled to the tissue measurement site. Methods and apparatus for placing the fluid are presented, thus minimizing sampling errors due to mechanical tissue distortion, specular reflectance, probe placement, and/or mechanically induced sample site stress/strain. The system is optionally automated.

DETAILED DESCRIPTION OF THE INVENTION

Sampling is controlled in order to enhance analyte concentration estimation derived from noninvasive optical sampling. More particularly, sampling is controlled using controlled fluid delivery to a region between a tip of a sample probe and a tissue measurement site. The controlled fluid delivery enhances coverage of a skin sample site with the thin layer of fluid. Means for controlling the fluid placement, temperature, coverage, and thickness are described, infra.

Herein, examples of coupling of a sample probe tip of a noninvasive glucose concentration analyzer to a skin sample site are used. However, the invention is generally used in coupling of an optical sampling device to skin.

Coordinate System

Herein, an x, y, and z-coordinate system relative to a given body part is defined. An x,y,z-coordinate system is used to define the sample site, movement of objects about the sample site, changes in the sample site, and physical interactions with the sample site. The x-axis is defined along the length of a body part and the y-axis is defined across the body part. As an illustrative example using a sample site on the forearm, the x-axis runs between the elbow and the wrist and the y-axis runs across the axis of the forearm. Similarly, for a sample site on a digit of the hand, the x-axis runs between the base and tip of the digit and the y-axis runs across the digit. Together, the x,y-plane tangentially touches the skin surface, such as at a sample site. The z-axis is defined as orthogonal to the plane defined by the x- and y-axes. For example, a sample site on the forearm is defined by an x,y-plane tangential to the sample site. An object, such as a sample probe, moving along an axis perpendicular to the x,y-plane is moving along the z-axis. Rotation or tilt of an object about one or a combination of axis is further used to define the orientation of an object, such as a sample probe, relative to the sample site. Tilt refers to an off z-axis alignment of the longitudinal orientation of the sample probe where the longitudinal axis extends from the sample probe tip interfacing with a sample site to the opposite end of the sample probe. A sample probe moving perpendicular to the sample site may move along the z-axis; however, if the local geometry of the skin of the sample site is tilted, then perpendicular movement of a sample probe refers to the sample probe moving normal to the skin surface, which may be on an axis that is not the z-axis.

Analyzer

Figure 1:
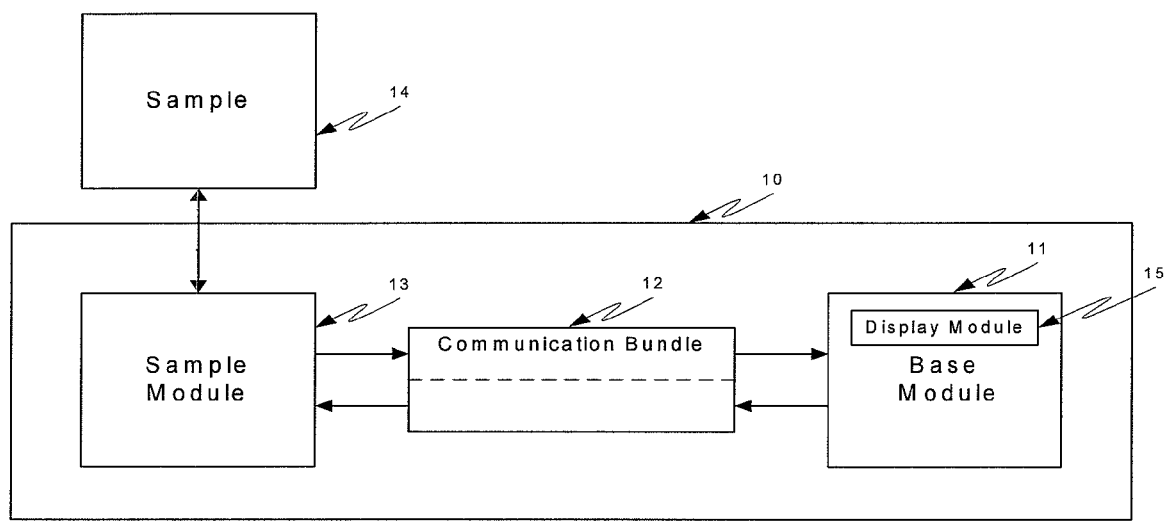
FIG. 1 presents an analyzer comprising a base module, a sample module, and communication means.

In many embodiments of the invention, an analyzer or a glucose tracking system is used. Referring now to FIG. 1, a block diagram of a spectroscopic analyzer 10 including a base module 11 and sample module 13 connected via communication means 12, such as a communication bundle is presented. The analyzer preferably has a display module 15 integrated into the analyzer 10 or base module 11. In one embodiment, the analyzer is a glucose concentration analyzer that comprises at least a source, a sample interface, at least one detector, and an associated algorithm.

Conventionally, all of the components of a noninvasive glucose analyzer are included in a single unit. Herein, the combined base module 11, communication bundle 12, sample module 13, and processing center are referred to as a spectrometer and/or analyzer 10. Preferably, the analyzer 10 is physically separated into elements including a base module in a first housing 11, a communication bundle 12, and a sample module in a second housing 13. Advantages of separate units include heat, size, and weight management. For example, a separated base module allows for support of the bulk of the analyzer on a stable surface, such as a tabletop or floor. This allows a smaller sample module to interface with a sample, such as human skin tissue. Separation allows a more flexible and/or lighter sample module for use in sampling by an individual. Additionally, separate housing requirements are achievable for the base module and sample module in terms of power, weight, and thermal management. In addition, a split analyzer results in less of a physical impact, in terms of mass and/or tissue displacement, on the sample site by the sample module. The sample module, base module, communication bundle, display module, and processing center are further described, infra. Optionally, the base module 11, communication bundle 12, and sample module 13 are integrated into a single unit.

Sample Module

A sample module 13, also referred to as a sampling module, interfaces with a tissue sample at a sample site, which is also referred to as a sampling site. The sample module includes a sensor head assembly that provides an interface between a glucose concentration tracking system and the patient. The tip of the sample probe of the sample module is brought into contact or proximate contact with the tissue sample. Optionally, the tip of the sample probe is interfaced to a guide, such as an arm-mounted guide, to conduct data collection and removed when the process is complete. An optional guide accessory includes an occlusion plug that is used to fill the guide cavity when the sensor head is not inserted in the guide, and/or to provide photo-stimulation for circulation enhancement. In one example, the following components are included in the sample module sensor head assembly: a light source delivery element, a light collection optic and an optional fluid delivery channel from a reservoir through a portion of the sample probe head to the sample probe head skin contact surface. Preferably, the sample module is in a separate housing from the base module. Alternatively, the sample module is integrated into a single unit with the base module, such as in a handheld or desktop analyzer. The sample module optionally has a pressure sensor generating a charge and corresponding voltage indicative of contact pressure. For example, a film with air voids internally contained results in different capacitive charges being measured between film layers as the layers are pressed together, as a measure of pressure on the probe tip surface. An example is an Emfit film (Emfit Ltd, Finland).

Communication Bundle

A communication bundle 12 is preferably a multi-purpose bundle. The multi-purpose bundle is a flexible sheath that includes at least one of:

electrical wires to supply operating power to the lamp in the light source;
thermistor wires;
one or more fiber-optics, which direct diffusely reflected near-infrared light to the spectrograph;
a tube, used to transport coupling fluid and/or optical coupling fluid from the base unit, through the sensor head, and onto the measurement site;
a tension member to remove loads on the wiring and fiber-optic strand and/or to moderate sudden movements; and
photo sensor wires.

Further, in the case of a split analyzer the communication bundle allows separation of the mass of the base module from the sample module. In another embodiment, the communication bundle is in the form of wireless communication. In this embodiment, the communication bundle includes a transmitter, transceiver, and/or a receiver that are mounted into the base module and/or sample module.

Base Module

A portion of the diffusely reflected light from the sample site is collected and transferred via at least one fiber-optic, free space optics, or an optical pathway to the base module. For example, a base module contains a spectrograph. The spectrograph separates the spectral components of the diffusely reflected light, which are then directed to a photo-diode array (PDA). The PDA converts the sampled light into a corresponding analog electrical signal, which is then conditioned by the analog front-end circuitry. The analog electrical signals are converted into their digital equivalents by the analog circuitry. The digital data is then sent to the digital circuitry where it is checked for validity, processed, and stored in non-volatile memory. Optionally, the processed results are recalled when the session is complete and after additional processing the individual glucose concentrations are available for display or transfer to a personal computer. The base module also, preferably, includes a central processing unit or equivalent for storage of data and/or routines, such as one or more calibration models or net analyte signals. In an optional embodiment, a base module includes one or more detectors used in combination with a wavelength selection device, such as a set of filters, Hadamard mask, and/or a movable grating.

Display Module

A noninvasive glucose concentration analyzer preferably contains a display module 15 that provides information to the end user or professional. Preferably, the display module 15 is integrated into the base module 11. Optionally, the display module is integrated into the sample module 13 or analyzer 10. The display screen communicates current and/or historical analyte concentrations to a user and/or medical professional in a format that facilitates information uptake from underlying data. A particular example of a display module is a 3.5" ¼ VGA 320×240 pixel screen. The display screen is optionally a color screen, a touch screen, a backlit screen, or is a light emitting diode backlit screen.

Tissue Stress/Strain

Preferably, a controller moves a sample targeting probe and/or a sample probe so as to make minimal, controlled, and/or proximate contact with a sample tissue to control stress and/or strain on the tissue, which is often detrimental to a noninvasive analyte property estimation. Strain is the elongation of material under load. Stress is a force that produces strain on a physical body. Strain is the deformation of a physical body under the action of applied force. In order for an elongated material to have strain there must be resistance to stretching. For example, an elongated spring has strain characterized by percent elongation, such as percent increase in length.

Skin contains constituents, such as collagen, that have partially elastic spring-like properties. That is, elongation causes an increase in potential energy of the skin. Strain induced stress changes optical properties of skin, such as absorbance and scattering. Therefore, it is not desirable to make optical spectroscopy measurements on skin with varying stress states. Stressed skin also causes fluid movements that are not reversible on a short timescale. The most precise and repeatable optical measurements are therefore conducted on skin in the natural strain state, such as minimally or non-stretched stretched skin. Skin is stretched or elongated by applying loads to skin along any of the x-, y-, and z-axes. Controlled contact reduces stress and strain on the sample. Reducing stress and strain on the sample results in more precise sampling and more accurate and precise glucose concentration determinations.

Effect of Displacement on Tissue Spectra

The displacement of a tissue sample by a sample probe results in compression of the sample site. The displacement results in a number of changes including at least one of:
- a change in the localized water concentration as fluid is displaced;
- a change in the localized concentration of chemicals that are not displaced such as collagen; and
- a correlated change in the localized scattering concentration.

In addition, physical features of the sample site are changed. These changes include at least one of:
- compression of the epidermal ridge;
- compression of the dermal papilla;
- compression of blood capillaries;
- deformation of a skin layer;
- deformation of skin collagen; and
- relative movement of components embedded in skin.

Chemical and physical changes are observed with displacement of the sample probe into the tissue sample. The displacement of tissue is observed in spectra over a wide range of wavelengths from about 1100 to 1930 nm. The displacement of tissue also effects a number of additional skin chemical, physical, and structural features as observed optically.

An example of using light to measure a physical property, such as contact, stress, and/or strain, in tissue is provided. Incident photons are directed at a sample and a portion of the photons returning from the sample are collected and detected. The detected photons are detected at various times, such as when no stress is applied to the tissue and when stress is applied to the tissue. For instance, measurements are made when a sample probe is not yet in contact with the tissue and at various times when the sample probe is in contact with the tissue, such as immediately upon contact and with varying displacement of the sample probe into the tissue. The displacement into the tissue is optionally at a controlled or variable rate. The collected light is used to determine properties. One exemplary property is establishing contact of the sample probe with the tissue. A second exemplary property is strain. The inventors determined that different frequencies of light are indicative of different forms of stress/strain. For example, in regions of high water absorbance, such as about 1450 nm, the absorbance is indicative of water movement. Additional regions, such as those about 1290 nm, are indicative of a dermal stretch. The time constant of the response for water movement versus dermal stretch is not the same. The more fluid water movement occurs approximately twenty percent faster than the dermal stretch. The two time constants allow interpretation of the tissue state from the resultant signal. For instance, the interior or subsurface hydration state is inferred from the signal. For instance, a ratio of responses at high absorbance regions and low absorbance regions, such as about 1450 and 1290 nm, is made at one or more times during a measurement period. Changes in the ratio are indicative of hydration. Optionally, data collection routines are varied depending upon:
- the determined state of the tissue; and/or
- an observed tissue transient.

For example, the probing tissue displacement is varied with change in hydration or determined thickness of a skin layer, such as the dermal layer. The strain measurement is optionally made with a sample state probing system, a targeting system, or an optical measurement system. Tissue state probes describe herein are optionally used in conjunction with a dynamic probe, described infra.

A fluid, such as a coupling fluid, is preferably applied between the tip of the sample probe and the tissue sample site. It is determined that a highly viscous coupling fluid degrades the noninvasive analyte determination system. A highly viscous coupling fluid requires increased pressure from movement of a sample probe tip to a tissue sample site in order to displace the viscous coupling fluid. For example, Fluorolube is a viscous paste that is not readily displaced. The pressure required for the tip of the sample probe to displace the Fluorolube results in tissue stress and strain that degrades the analytical quality of the noninvasive signal. Therefore, less viscous coupling fluids are required, such as FC-70 or FC-40. The viscosity of the coupling fluid should not exceed that of FC-70 and preferably the viscosity of the coupling fluid should not exceed that of FC-40.

Coupling Medium

The interface between an optical probe and a skin surface at the tissue measurement site is potentially a significant source of sampling error. There are a number of distinct, but inter-relating, sampling issues including:
- induced tissue stress/strain observed in collected optical signal;
- skin surface irregularity;
- air gaps; and
- refractive index mismatch.

Fluid use between a sample site and an interfacing sample probe surface is useful for a number of reasons. First, fluid allows for optical contact between a sample probe tip surface and a sample site with reduced pressure or displacement of the tissue by the probe tip. This results in reduced stress/strain. Second, coupling fluid aids in reduction of surface reflection due to optical aberrations in surface coupling and stretching of the surface tissue due to sample probe contact. Third, coupling fluid use aids in stabilizing hydration of surface tissue. Fourth, a refractive index matching coupling fluid enhances light throughput into the tissue and light collection from the tissue.

Stress/Strain

Sampling induced stress/strain is described, supra.

Skin Surface Irregularity

Skin surface irregularity results in an increase in the surface reflection of incident light. Basically, incident light normal to the surface penetrates into the skin sample based upon the difference in refractive index according to Snell's Law. For the refractive index of skin, approximately 1.38, and the refractive index of air, approximately 1.0, approximately 4% of the light will be reflected and 96% of the light will penetrate into the skin. The surface irregularities of skin mean that the incident light is not normal to the surface. This results in more reflected light, and less penetrating light.

Tissue Hydration

Air gaps near the skin surface complicate near infrared spectra interpretation. Some light penetrating into an outermost layer of skin hits an air pocket. Some light is reflected off of each surface of the air pocket. Many air pockets or poor hydration leads to a significant reduction in the percentage of incident photons that penetrate through the outermost skin layers, such as the stratum corneum, to the inner skin layer.

Refractive Index

The refractive index mismatch and Snell's Law explain part of the effects described for the skin surface irregularities and air gaps. However, the inventors have determined that a coupling fluid need not be a refractive index matching fluid, also known as an optical coupling fluid, in order to increase usable light throughput. For example, in the case of a high refractive index material, such as a lens, coming into contact with skin via a coupling fluid, the coupling fluid need not have a refractive index between that of skin and the optic in order to be beneficial. For example, the percentage of incident photons passing through a silicon lens into skin is increased even with use of a coupling fluid that does not have a refractive index between that of silicon and skin. For example, a fluorocarbon, such as FC-40 manufactured by 3M Corporation, (St. Paul, Minn.) has an index of refraction of 1.290 that is not between that of skin, 1.38, and silicon, approximately 2. However, the FC-40 still increases incident photon penetration by displacement of air. Specifically, for coupling silicon and skin FC-40 is not an "index-matching medium", "optical coupling fluid", or "refractive-index matching coupling fluid"; however, it still aids in light coupling by displacing the lower refractive index air. Alternatively, a coupling fluid, such as a chlorofluorocarbon with a higher index of refraction, is called an index-matching medium. A chlorofluorocarbon with an index of refraction between that of the coupling medium and the skin will increase the number of penetrating photons due to both index of refraction matching and displacement of the air that results in a smoother surface.

Table 1 provides index of refractions for a series of chlorohydrocarbons where it is observed that as the number of chlorine atoms increases, the refractive index increases. Longer chain chlorocarbons have higher refractive indices. Table 2 demonstrates that as the substituted halide atom increases in atomic number, the refractive index increases. Combining the information from Tables 1 and 2, it is observed that the minimum refractive index for a chlorohydrocarbon is 1.3712 and that the minimum refractive index for a non fluorohydrocarbon is 1.3712.

TABLE 1

Chlorocarbons and chlorohydrocarbons

| Molecule | Refractive Index |
|---|---|
| $CH_3Cl$ | 1.3712 |
| $CH_2Cl_2$ | 1.4244 |
| $CHCl_3$ | 1.4476 |
| $CCl_4$ | 1.4607 |

TABLE 2

Halohydrocarbons

| Molecule | Refractive Index |
|---|---|
| $CH_2Cl_2$ | 1.4244 |
| $CH_2Br_2$ | 1.5419 |
| $CH_2I_2$ | 1.7425 |

Viscosity

A fluid between a sample probe tip surface and a tissue sample beneficially has a kinematic viscosity that allows rapid movement of the fluid from between the sample probe tip and the sample site when the tip is brought into proximate contact or contact with the tissue sample. Fluorocarbons have kinematic viscosities fulfilling the requirement. In particular, FC-40 has a kinematic viscosity of 2.2 centistokes (cs). Longer chain fluorocarbons, such as FC-70 with a viscosity of 12 cs is borderline acceptable. Generally, the fluorocarbon should have a viscosity of less than about 12 cs and preferably less than about 5 cs.

Reflection

Coupling the relatively smooth surface of an optical probe with the irregular skin surface leads to air gaps between the two surfaces. The air gaps create an interface between the two surfaces that adversely affects the measurement during sampling of tissue due to refractive index considerations as described, infra. A coupling medium is used to fill these air gaps. Preferably, for an application, such as noninvasive glucose concentration estimation, the coupling fluid:

is spectrally inactive;
is non-irritating
is nontoxic;
has low viscosity for good surface coverage properties;
has poor solvent properties with respect to leaching fatty acids and oils from the skin upon repeated application; and
is thermally compatible with the measurement system.

It is possible to achieve these desirable characteristics by selecting the active components of the coupling fluid from the classes of compounds called fluorocarbons, perfluorocarbons, or those molecules containing only carbon and fluorine atoms. Nominally limiting chain length to less than 20, 18, or 16 carbons provides for a molecule having the requisite viscosity characteristics. Generally, smaller chain lengths are less viscous and thus flow over the sample surface more readily. Longer chains are more viscous and tend to coat the sample surface with a thicker layer and run off of the sample site over a longer period of time. The molecular species contained in the perfluorocarbon coupling fluid optionally contain branched, straight chain, or a mixture of both structures. A mixture of small perfluorocarbon molecules contained in the coupling fluid as polydisperse perfluorocarbons provides the required characteristics while keeping manufacturing costs low. Additives are optionally added to the fluid.

In one embodiment, the coupling fluid is a perfluoro compound, such as those known as FC-40 and FC-70, manufactured by 3M Corporation (St. Paul, Minn.). This class of compounds is spectrally inactive in the near-infrared region, rendering them particularly well suited for sampling procedures employing near-infrared spectra. Additionally, they have the advantage of being non-toxic and non-irritating, thus they can come into direct contact with living tissue, even for extended periods of time, without posing a significant health risk to living subjects. Furthermore, perfluoro compounds of this type are hydrophobic and are poor solvents; therefore they are unlikely to absorb water or other contaminants that will adversely affect the resulting optical sample. It is preferable that the sampling fluid be formulated without the addition of other substances, such as alcohols or detergents, which may introduce artifacts into the optical sample. Finally, the exceptional stability of perfluoro compounds eliminates the environmental hazard and toxicity commonly associated with chlorofluorocarbons.

Other fluid compositions containing both perfluorocarbons and chlorofluorocarbons are also suitable as coupling fluids: for example a blend of 90% polymeric chlorotrifluoroethylene and 10% other fluorocarbons have the desired optical characteristics. Chlorotrifluoroethene is optionally used. While these compositions containing both fluorocarbons and chlorofluorocarbons have the desired optical characteristics, their toxicity profiles and their solvent characteristics render them less desirable than the previously described fluorocarbons.

Additionally, other fluid media are suitable for coupling of an optical probe to a tissue measurement site, for example, skin toner solutions or alpha hydroxy-acid solutions.

Operation

During use, a quantity of sampling fluid is placed at the interface of the tissue measurement site and the fiber optic probe so that the tissue measurement site and the fiber optic probe are coupled leaving no or minimal air spaces between the two surfaces. Several methods of delivery sequence are described, infra.

In one method of coupling the interface of a tissue measurement site and a tip of a sample probe, a small amount of coupling fluid is placed on the skin surface prior to placing the fiber optic probe in close proximity or in contact with the sample site.

Another method of coupling the interface of a tissue measurement site and a tip of a sample probe is to place coupling fluid on the tip of the sample probe and bringing the sample probe into contact with a surface proximate the skin sample site.

Yet another method of coupling a tissue measurement site to an analyzer is to spray the tissue sample site with the coupling fluid and/or to spray the tip of the sample module and/or bundle prior to bring the sample into contact or close proximity with the analyzer.

An additional method of coupling a measurement site to a tip of a sample module is to deliver the coupling fluid while the tip of the sample module is in motion. For example, coupling fluid is delivered through small tubes that terminate at the tip of the sample module near the area of photon delivery and/or near the area of photon collection. For example, a fluorocarbon is dropped onto the tissue sample site through tubes terminating next to a central collection fiber.

In still yet another method of coupling a tissue measurement site and a tip of a sample probe, channels or ridges are provided that allow excess coupling fluid to be pushed out of the way or to drain off through gravity. A primary intent of this embodiment is to prevent applying undue pressure to the sample site when the tip of the sample probe is brought into close proximity and/or contact with the sample site. Pooling of excess coupling fluid is prevented by these channels. For example, a hydraulic effect created by the sample module pressing on coupling fluid on its way to the sample site is relieved by having channels through which excess coupling fluid freely flows when pressurized.

Another method of coupling the interface between the tissue measurement site and the tip of a sample probe is to first bring the tip of the sample probe into contact with the sample site, remove the sample probe from the sample site, deliver the coupling fluid, and then again bring the sample probe into close proximity with the sample site. This method eases locating the skin when a movable sample probe is used as described in U.S. patent application Ser. No. 11/117,104, filed Apr. 27, 2005, which is incorporated herein in its entirety by this reference thereto. In addition, the elapsed period of time between coupling fluid delivery and optical sampling, also known as the measurement, is minimized thus reducing the risk of evaporation of the coupling fluid prior to sampling. Exemplary elapsed times include less than about 30, 20, 10, or 5 seconds.

Still another method is to pull a partial vacuum on or about a tissue sample site. For example, the tip of an optical probe is pulled away from the sample site after making contact. In a second example, the tip of tubing filled with a coupling fluid is in contact with a sample site and fluid is withdrawn from the tubing or is backed off from the tip of the tubing. This movement of the coupling fluid creates a partial vacuum. Creating a partial vacuum creates a small convex tissue meniscus. Fluid, such as interstitial fluid, flows into the meniscus. This results in increased concentration of the analytical target of interest in the sampled optical tissue. Alternatively, applying a small negative pressure reduces a negative meniscus making the sample more readily sampled with a flat optical surface.

Yet another method of applying coupling fluid to a tissue site is to warm the coupling fluid to a target temperature prior to application. Examples of target temperatures include about 88, 90, 92, 94, 96, and 98 degrees Fahrenheit. Optionally, the tip of the sample probe and/or surface of the sample site are adjusted to or toward this first target temperature or to their own target temperature. Preferably, the two target temperatures are the same in order to reduce sampling variations resulting from temperature variation. A variation is to independently control or not control the sample site, coupling optic, and coupling fluid temperature.

Still yet another method of applying coupling fluid includes a step of removing coupling fluid from the sample site. Methods of removal include: waiting for a period of time to allow evaporation, allowing gravity induced run off of the fluid, and/or wiping off with a material, such as an absorbent cloth or wipe.

An additional method of providing a coupling fluid between a tissue site and an optical probe is to apply coupling fluid multiple times. For example, about one to ten microliters of coupling fluid is applied two or more times.

Optionally, coupling fluid is used to clean a sample site. For example, coupling fluid is applied to the sample site and removed as above in order to remove sample debris.

Yet another method of providing coupling fluid between a tip or an end of a sample probe and a tissue site or sample site is to determine contact of a z-axis movable sample probe tip from a response signal, such as a pressure sensor, a response from a broadband source, or from a response to a photons emitted from a light emitting diode. For example, a light emitting diode is optionally used outside of the range detected by detectors coupled to a broadband source element in a sample module. For instance, the light emitting diode wavelength is centered at a spectral feature, such as due to water, fat, or protein, or within an optical window such as in the 'H', 'J', or 'K' band regions of the electromagnetic spectrum. An additional detector element is optically associated with the light emitting diode. For instance, a broadband source is used in conjunction with a grating from about 1100 to 1800 nm. A light emitting diode and its associated detector are used outside of the detected broadband source region to detect, through intensity change, contact of a sample probe, analyzer, or sample probe tip with a tissue sample. Particular water absorbance features that are optionally used occur at about 1900, 2000, or 2500 nm.

Furthermore, certain non-fluid media having the requisite optical characteristic of being near-infrared neutral are also suitable as a coupling medium, for example, a GORE-TEX membrane interposed between the probe and the surface of the measurement site, particularly when used in conjunction with one of the fluid media previously described.

Localized Delivery

Preferably, coupling fluid covers the entire sample site prior to sampling. Volume requirements for the various modes of delivery for a sample are small, such as less than about fifty microliters. Preferably about five to thirty microliters of coupling fluid are applied to the sample site. For a sample site of about two to six millimeters in diameter, eight plus or minus one to two microliters is typically sufficient. Precision and/or accuracy of volume of delivery is important in order to avoid excess waste, sufficient coverage, and/or undue pooling. Excess fluid results in optically observed stress/strain, which degrades analyte measurement, when the fluid is displaced by bringing a sample probe head into contact with a sample site through displacement of the fluid. The target volume of delivery is dependent upon the sample probe geometry and size.

In one embodiment, a driving force is applied to a fluid, such as a coupling fluid or optionally an optical coupling fluid. The driving force delivers the fluid delivers fluid at and/or near the sample site. As described herein, a number of driving force methods of delivery exist including: via spraying, dribbling, misting, through a gravity feed system, via capillary action, via a peristaltic pump, or driven by a motor or a piston. Preferably, the fluid is delivered at the sample site in a controlled and/or automated manner.

Microfluidic Channel

Figure 2:
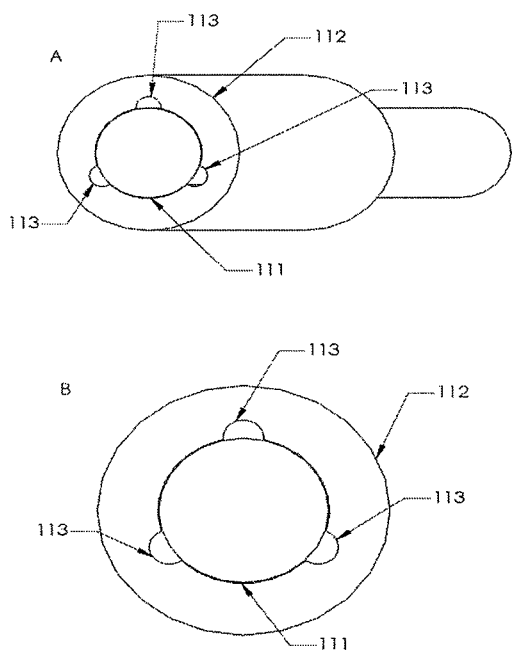
FIG. 2 provides (A) a perspective view and (B) an end view of a fluid delivery system.

Referring now to FIGS. 2A and 2B, an exemplary embodiment of fluid delivery is presented. FIGS. 2A and 2B present a perspective and end view of one embodiment of a fluid delivery system, respectively. One or more microfluidic channels or lumens 113 are localized about a central optic 111 in a sample probe. The microfluidic channel is a tube or tubular opening, canal, duct, or cavity. The lumens or microfluidic channels 113 are optionally of any geometric shape, such as a circle, oval, triangle, square, or other polygonal shape. The lumens are either in contact with the central optic 111, are embedded in a coating material 112, or are located in close proximity to the coating material 112. Preferably, the lumens are extruded or co-extruded for ease of manufacture. An example of a central optic is a core, cladding, and optional buffer of a fiber optic. The microfluidic channel allows passage of a fluid through the sample probe tip to the sample site. Preferably, the fluid is delivered at a multitude of sites circumferentially distributed about a central sample site area, such as about a central collection fiber optic. Circumferential delivery of fluid enhances surface coverage of the sample site by the fluid. For example, a dense fluid, such as a fluorocarbon, travels with gravity. On a slanted surface, such as a skin sample site, delivery of the fluorocarbon on only one side of the sample site results in poor or no coverage of the sample site when gravity pulls the fluid downhill away from the sample site. Delivery of the fluid at multiple points around the sample site allows coverage of the sample site for any non-level orientation of the sample site. The number of lumens in this example is optionally one or more. For example, two, four, or six lumens are used to deliver a coupling fluid to the sample site. The use of a larger number of lumens helps to insure coverage of the sample site by the coupling fluid.

Fluid Delivery Channel

In yet another embodiment, a sample probe having a tip is presented where the sample probe tip has one or more channels in the surface. When the sample probe is in contact with a skin sample site, the channels form one or more tunnels with each tunnel being completed by the skin at the sample site. The channels are used as a low resistance flow conduit for a fluid, such as a coupling fluid. The channels enhance delivery of the fluid across the sample probe tip about a sample interface sampling site. The fluid readily travels through one or more channels about the sample probe surface. The channels provide a pathway for rapid delivery of the fluid with minimal applied pressure from the fluid movement being delivered to the skin surface. Capillary action then distributes the fluid from the channel to the remaining surface of the sample probe tip to substantially cover the optically sampled region.

Figure 3:
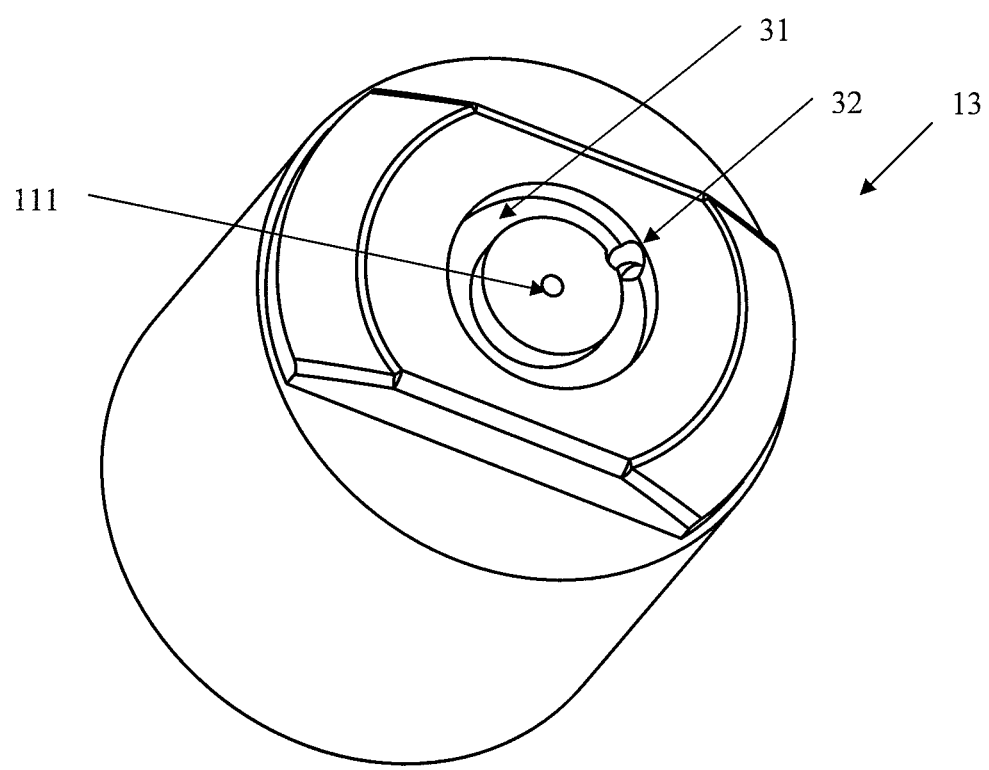
FIG. 3 illustrates a sample probe tip with a channel for fluid delivery.

Referring now to FIG. 3, an example of a sample probe 13 head having a channel 31, such as a moat shape about a central collection optic 111, is presented. A moat is used to distribute fluid circumferentially about the sample site. Preferably, the channel has an internal hole 32 through which coupling fluid is actively delivered or actively withdrawn from the moat. Fluid is delivered to the moat through the internal hole 32 to the sample probe tip from a reservoir. The fluid is optionally temperature controlled prior to delivery to the sample site. Examples of control temperatures are about 88 to 100 degrees Fahrenheit or about 90 to 92 degrees Fahrenheit.

In one example of fluid delivery using a channel, such as a moat, fluid is:
(1) delivered to the channel;
(2) distributed through the channel;
(3) allowed to cover the optically sampled site via capillary action or through delivery of excess volume in combination with a small delivery force.

Optionally, prior to optical sampling, a partial vacuum is used to withdraw excess fluid leaving a thin film of the fluid evenly coated on and about the sample site.

The partial vacuum holds the skin sample against the sample probe tip resulting in direct intimate contact between the sample probe tip and the skin sample site through a thin film of fluid, such as (1) a coupling fluid or (2) an optical coupling fluid. The partial vacuum is maintained at small negative relative pressure to ensure low strain of the tissue at the optical sample site.

There exist a number of benefits of a channel. A channel scavenges excess fluid during the measurement process. Extra fluid on the sample site has at least two negative impacts. First, too much fluid on the sample site allows incident light to reflect between the skin and the sample probe head surface to a detection optic resulting in light, having properties not unlike specularly reflected light, that has not entered into the skin sample site with corresponding interaction with the analyte of interest. This light degrades analyte measurement. Second, excess fluid on the sample site is displaced as the sample probe surface is brought into proximate contact with the sample site. Since fluid has a resistance, the displacement of the fluid results in stress/strain on the sample site. Thus, a channel for removal of excess fluid results in a higher signal due to a higher percentage of detected photons having interacted with the analyte of interest and a reduced noise due to the reduction of stress/strain induced spectral signals. A channel is filled or partially filled actively, such as with a pump, or passively, such as through a gravity flow.

A channel is optionally filled or partially filled with a fluid through:
  an internal hole after contact of the sample probe head with the skin;
  through application of fluid to the sample probe head surface with subsequent contact with skin;
  through application of fluid to the sample site with subsequent contact with the sample probe head;
  from capillary action of fluid after the sample probe head is already in contact with the sample site; or
  any combination of the above.

Moat

Figure 4:
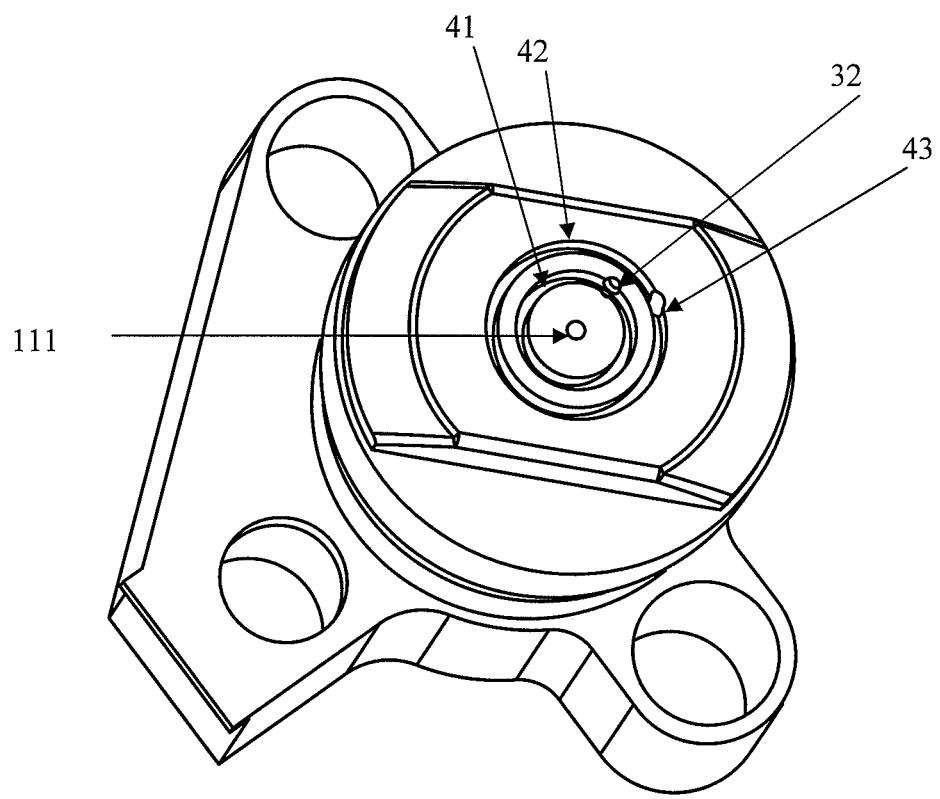
FIG. 4 illustrates a sample probe tip with multiple channels for fluid delivery.

Referring now to FIG. 4, an example of a sample probe head having an inner moat 41 shaped channel and an outer moat 42 shaped channel about a central collection optic is presented. Preferably, delivery of fluid through an opening 32 into the inner channel is performed. Optionally, the opening 32 is used to fill fluid into both the inner moat and outer moat or just via a second opening 43 to the outer moat. One purpose of the outer moat is to minimize air being drawn into the center optic when the inner moat has a partial vacuum applied to it. When the reduced pressure partial vacuum is applied, the outer moat serves as a seal at least partially filled with the fluid. Generally, any number of channels or moats on the sample probe head may be used depending upon the specific fluid distribution patterns and timing of fluid delivery requirements and the center optic is alternatively one or more optics or bundlets terminating on the sample probe face.

Radial Channel

In still another embodiment, a sample probe head having channels running radially outward from a central collection optic is used. Fluid is delivered to the sample site as described, supra. Preferably, fluid is delivered through two or more internal holes leading from a fluid reserve to two or more channels. The radial distribution of channels has several benefits. First, the radial distribution of channels enhances fluid delivery over and around the optically sampled skin tissue. Second, the distance of required capillary action of the fluid between the sample probe tip and the sample site is minimized. This enhances complete coverage of the sample site with the fluid and minimizes time requirements for capillary action coverage of the sample site. Third, one or more of the radially extending channels allow an escape path for excess fluid. The escape path reduces optically observed stress/strain tissue site stress strain as reduced pressure is applied to the sample site when:
  fluid is forced through a delivery hole, excess pressure of fluid delivery is relieved through the escape channel; and/or
  force is applied to the fluid as a result of bringing into proximate contact the sample probe head surface and the skin sample site.

In yet another example, a sample probe head having a combination of channel types is presented. In this example, a moat channel is used in combination with channels extending along an axis. Preferably, the axis of extending channels is along a long axis of the sample site body part, such as along an x-axis substantially defined by an elbow and wrist of an arm. The gently sloping skin along an x-axis of an arm will inherently stay in contact longer with the channel as opposed to the curved shape of the arm along a y-axis across the arm. The combination of channel types allows:
  distribution of fluid about a sample site;
  a pressure relief channel; and
  flow of fluid between interconnecting channels.

Generally, any number of channels and any geometric shape or distribution of channels on the sample probe head may be used depending upon the specific fluid distribution patterns and/or timing of fluid delivery requirements.

In yet another example, fluid is delivered to the sample site when there exists a thin spatial air gap between the sample probe tip surface and the sample site. For instance, a fluid is delivered in close proximity to a collection optic. The fluid contacting both the sample probe tip surface and skin will radiate outward as a result of capillary action. The radial movement of the fluid results in a negative pressure relative to standard atmospheric pressure. The negative pressure pulls the skin into proximate contact with the sample probe tip surface through a thin layer of the fluid. The minimal change in pressure delivers enough negative force to the skin to pull the skin into contact with the sample probe tip in an elastic process. The elastic nature of the force results in replicate measurement lacking an optically observed historesis effect due to being in a linear range of the visco-elastic tissue response. For example, fluid is delivered when a distance between the sample probe head surface and skin surface is:
  less than a drop diameter size of the fluid;
  at a distance of less than about 0.25 mm;
  at a distance of less than about 0.15 mm; and/or
  at a distance that creates an effective diameter, such that the resultant negative pressure is sufficient to draw into proximate contact the sample probe head surface and skin surface.

Hence, a method of fluid delivery is presented where the step of fluid delivery itself to the gap between a sample probe tip surface and skin sample site results in movement of the skin into proximate contact with the probe tip.

In yet another example, a transient response is used to determine a sampling protocol. For instance, a measure of a tissue transient to an applied force results in a measure of a tissue property, such as:
  an analyte containing dermal thickness;
  a resistance to tissue-compression;
  a bulk modulus;
  a bulk skin property such as
    a collagen density;
  a tissue layer, such as an analyte containing layer, resistance to compression; and
  an elastic range of tissue compression from an applied force.

The sampling protocol is then adjusted to the skin property. For instance, displacement of skin tissue by a sample probe tip as a result of z-axis movement is better tolerated for a skin sample having larger than normal collagen density or a thicker dermal layer. Conversely, a smaller z-axis movement of the sample probe tip is designated by control software when the opposite skin property is observed. The z-axis movement of the sample probe tip is thereby controlled to a depth resulting in sufficient contact pressure with the skin without collapse of the desired skin layer. The controlled subject dependent displacement of the probe into the skin yields one optically sampled skin volume for one skin property type and a second optically sampled skin volume for a second skin property type. Therefore, the mechanical sampling is optimized to the skin type based upon the transient tissue response to the applied force. In addition, the transient response is optionally used in selection of a corresponding calibration model. One calibration model is used for one skin type and a second calibration model is used for a second skin type. Each calibration yields enhanced analyte prediction performance as each model may more robustly focus on a narrow range of skin types.

Automated Delivery

An automated coupling fluid delivery system is used to deliver coupling fluid to a sample site with minimal human interaction. An automated coupling fluid delivery system provides many benefits including:
  accurate fluid delivery volume;
  precise fluid delivery volume;
  accurate fluid delivery location;
  precise fluid delivery location;
  software controlled delivery;
  delivery with minimal user input; and/or
  ease of use.

Delivery of coupling fluid to a sample site is preferably performed by a lay user in a convenient manner. Automated control of one or more of the delivery steps is therefore preferential as the task is simplified for the user and controls to the delivery are established by the apparatus.

Figure 5:
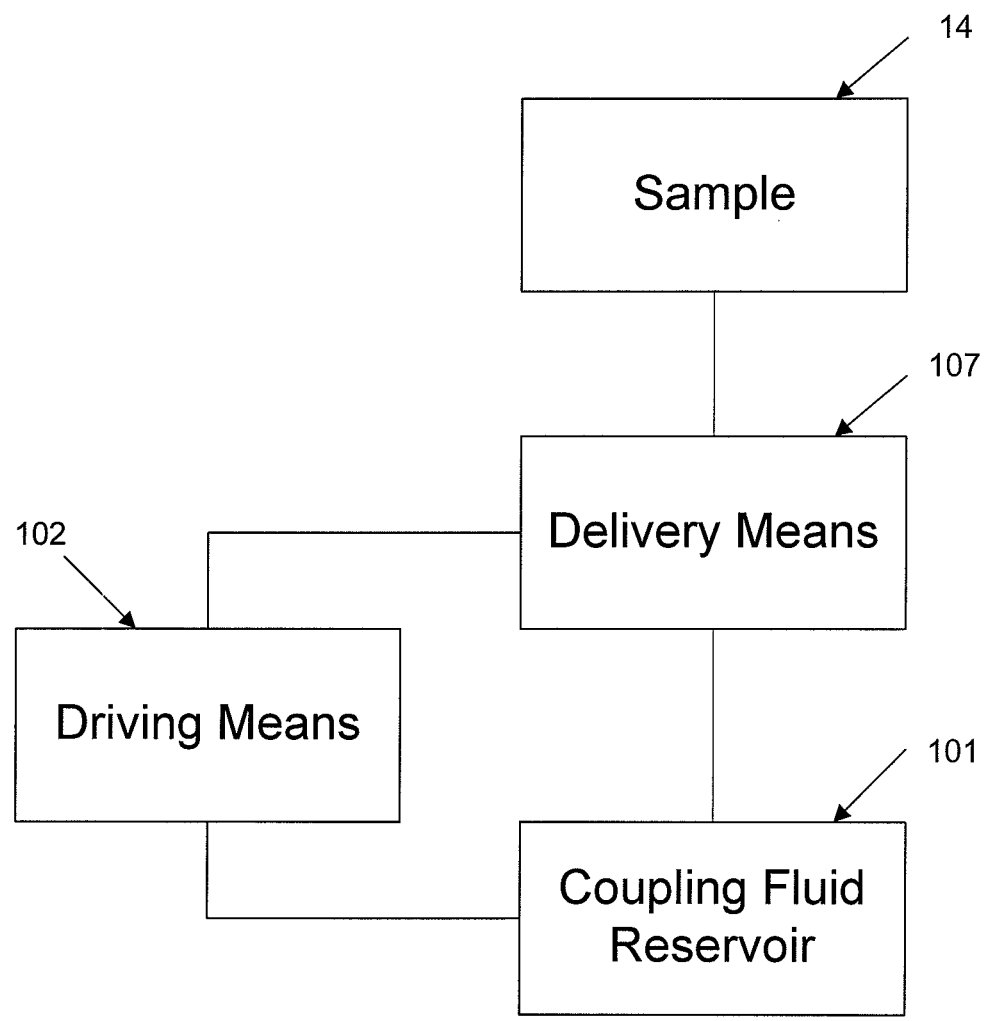
FIG. 5 provides a block diagram of fluid delivery to a sample site.

Referring now to FIG. 5, an example of a coupling fluid flow diagram is presented. A reservoir of coupling fluid 101 is moved to a sample site 14 via delivery means 107, such as tubing. Driving means 102 are used force the coupling fluid to the sample site 14. Examples of these elements are provided, infra.

Reservoir

A reservoir or container of coupling fluid is maintained so that a supply of coupling fluid is available for use with sampling. Maintaining a reservoir with the analyzer or having a reservoir integrated into the analyzer reduces the number of items that are independently handled by a user. This reduces the complexity of a noninvasive measurement and results in overall better performance in terms of accuracy and precision. Examples of reservoirs or containers include containers of various sizes, a syringe, a cartridge, a single use packet, a blister pack, a multiuse container, or a large auxiliary container. The reservoir is optionally a disposable or reusable. For instance, a small refillable reservoir is maintained within a sample module or within an analyzer. This allows, for example, the analyzer to be portable. In another instance, an external reservoir is coupled to the analyzer in either a permanent or removable fashion. Larger reservoirs are useful due to less frequent refilling requirements. Smaller reservoirs, such as a reservoir of less than one or two milliliters are still useful for multiple measurements as a preferred coupling fluid delivery volume is less than fifty microliters per use.

Delivery Means

Coupling fluid is moved from the reservoir to a sample site through delivery means, such as tubing, flexible tubing, or channels. The delivery means 107 optionally include a gate or a variable resistance flow section, especially when the housed reservoir is in close proximity to the sampling site. The coupling fluid is optionally routed through or integrated into a sample probe module. Optional routing through the sample module allows for delivery within close proximity to the sample site, such as within one inch. Delivery in an accurate area about a sample results in adequate coverage of the sample site while requiring less coupling fluid volume. For example, delivery near the sample site center allows about 5, 8, 10, 20, 30, or 40 microliters of coupling fluid to adequately cover the sample site. In addition, routing through the sample module allows movement of the sample module by a user to also control routing of the integrated delivery means without an additional action. In addition, the dual movement maintains tight control of the coupling fluid delivery to the sample site in terms or precision and accuracy of position of delivery. Precision and accuracy is further enhanced by the use of a guide coupling the sample module to the sample site. In an additional embodiment, the delivery channels or tubes run by thermal control means, such as a heat element, described infra. In still yet another embodiment, the delivery means 107 are thermally insulated.

Driving Means

Means are used to deliver coupling fluid to a sample site 14. Driving means 102 are available in a number of forms, such as via a motor, a solenoid, a gear, a piston, a peristaltic pump, gravity feed, capillary action, or a magnetic drive. Power supplying the driving means include potential energy, electrical sources, manual force, gravity, and magnetic fields. Driving means optionally push or pull the fluid. Further, driving means are optionally connected to the reservoir 101 or to the delivery means 107.

Several examples of fluid delivery systems are provided, infra.

EXAMPLE I

Referring now to FIG. 5, a block diagram of an automated coupling fluid delivery system is provided. A coupling fluid is held in a reservoir 101. This reservoir contains the fluid in a package that allows for ready transport, protection from contaminants, and on-time delivery. Fluid is forced from the reservoir by driving means 102 to force coupling fluid through tubing 107 to the sample site 14.

Figure 6:
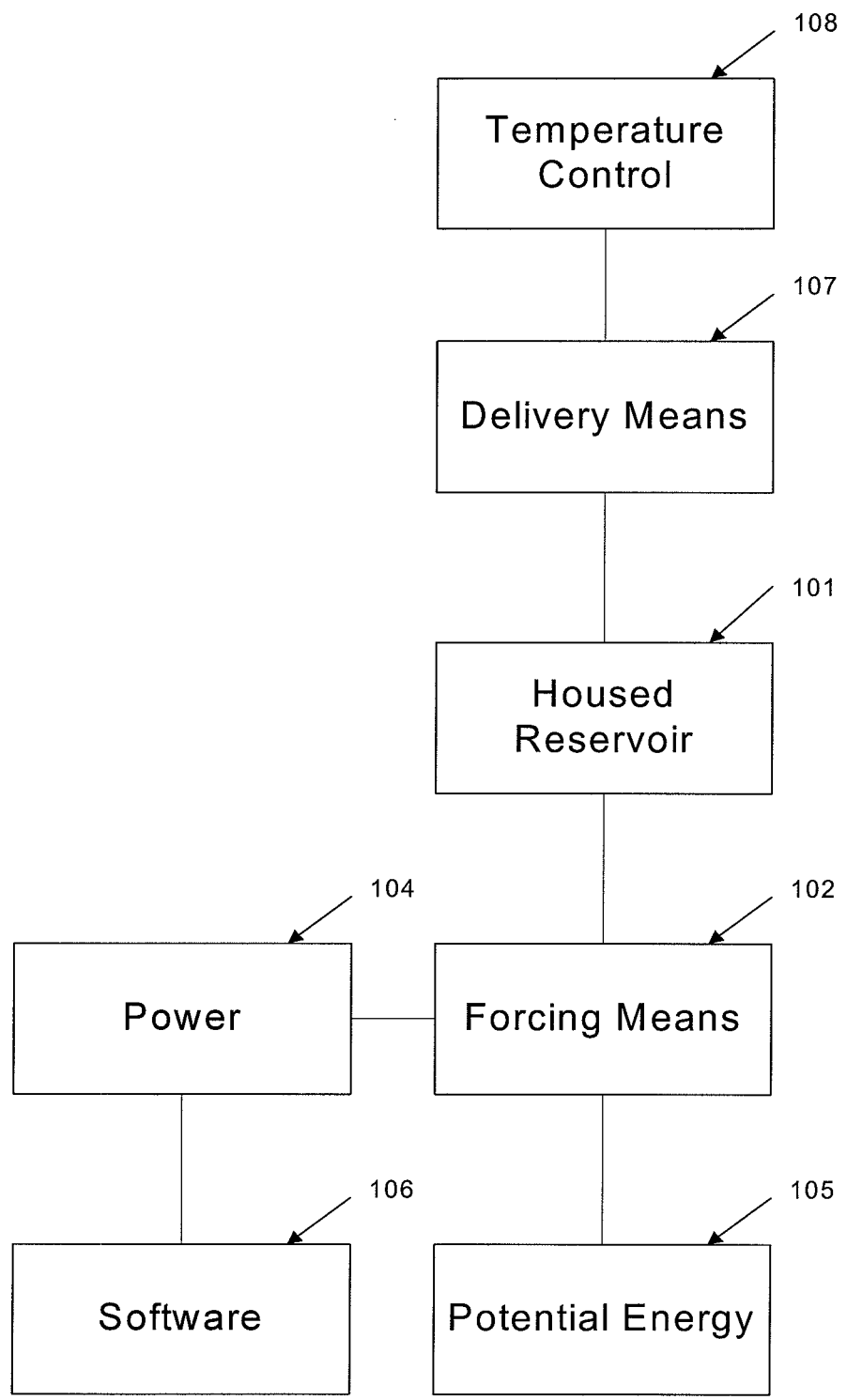
FIG. 6 provides a block diagram of fluid delivery to a sample site.

Referring now to FIG. 6, optional power supplies 104 are used for powering the driving means 102 and include gravity and/or manual, alternating current, or direct current power. Often, the driving forces required tax a power budget. An optional potential energy assist 105 is provided to minimize auxiliary power requirements. Examples of a potential energy source 105 include a coiled spring or compressed gas, infra.

Optional software 106 is used to control coupling fluid delivery. The software is preferably tied into a larger data acquisition system of an analyzer, such as a central processing unit of a noninvasive glucose concentration analyzer. The software is used in either an open-loop or closed loop format. For example, the software controls delivery of a predetermined volume of coupling fluid to the sample site. The fluid delivery is preferably controlled by software to deliver at a set time within a sampling sequence, such as just prior to sampling skin tissue 14. Optionally, delivery volumes and/or times are controlled through software in a closed-loop system that has sensor feedback. Sensors include an electrical contact sensor, a pressure sensor, and/or an optical signal, such as a response generated from a near-infrared spectrum. An example of an electrical contact sensor is a sensor where, upon contact of a sample probe tip with a body part of a subject, an electrical circuit is completed and a signal indicative of the circuit completion is generated.

EXAMPLE II

In a second example, coupling fluid is delivered through tubing to a sample site. After delivery the coupling fluid is backed off from the end of the tubing exit, such as by capillary action or by reversing a pushing force into a pulling force. For example, a motor pushing the fluid is reversed and the fluid is pulled back a distance into the tubing. A sensor is optionally placed across the tubing to determine the position of the meniscus of the coupling fluid in the tubing. For example, a light source, such as a light emitting diode, shines through the tubing and is sensed by a detector. As first air and then coupling fluid is moved past the sensor in the tubing, a change in light intensity is indicative of the meniscus and hence the position of the coupling fluid in the tubing. The dead volume of tubing past the detector is readily calculated. The driving means 102, such as a stepper motor, are then used to deliver the dead volume of coupling fluid plus the desired volume of coupling fluid to be delivered to the sample site 14. In this manner, the desired delivery volume of coupling fluid is delivered to the sample site 14. Optionally, the motor is computer controlled. Optionally, there is a feedback between the detector response to the motor that provides a closed loop system controlling the volume of coupling fluid. Optionally, analyzer control software controls when coupling fluid is to be delivered to the sample site, such as after tissue has been sensed by the analyzer, after a hardware or software indication by the user, or at appropriate times in any of the methods in the Operation section, supra.

EXAMPLE III

In a third example, a series of optical readings are collected by the analyzer. As the sample probe is brought into proximity to the sample site 14, the near-infrared reading changes. Features of the signal are indicative of the distance between the tip of the sample probe and the sample site. For example, the collected intensity at wavelengths of high absorbance decrease toward zero as the tip of the sample probe approaches a tissue sample. An example of a high absorbance feature is water at or about 1450 nm, 1900 nm, and/or 2600 nm. Correlation between intensity readings at one or more wavelengths and distance between the tip of the sample probe are used to provide feedback to the user or preferably to a z-axis moveable sample probe. The feedback allows the controller to move the sample probe relative to the tissue sample site. This allows, for example, controlling the probe to make contact with the sample, for the sample probe to be backed off from the sample, for a coupling fluid to be delivered to the sample site, and for the probe to be moved into close proximity to the sample probe, as described, supra. Examples of z-axis motor control of a sample module are described in U.S. provisional patent application No. 60/566,568, filed Apr. 28, 2004 which is incorporated herein in its entirety by this reference thereto. Optionally, the proximity between a tip of a sample module and a tissue site is determined with a pressure sensor placed on or near the tip of the sample probe of the analyzer. For example, contact is determined with the sensor or a proximate distance is determined by the feedback signal of the sensor.

EXAMPLE IV

In a fourth example, the sample probe is moved in a manner that does not make contact with the tissue sample. Instead, the algorithm moves the tip of the sample probe into close proximity to the tissue sample before or after coupling fluid delivery and proceeds to sample the tissue with a small gap between the tissue sample and the tip of the optical probe. In this manner, pressure effects are alleviated and the coupling fluid reduces specular reflection to allow precise and accurate noninvasive glucose concentration estimations using near-infrared spectra. Optionally, in this embodiment the pathlength of the coupling fluid between the tip of the sample probe and the tissue sample is determined from an interference pattern. This interference pattern is then used to control the distance between the tip of the sample module and the tissue sample to a fixed pathlength.

EXAMPLE V

In a fifth example, means are used to minimize formation of gaps in the delivery of coupling fluid to the sample site. For instance, air pockets or bubbles are preferably removed from a fluid delivery line. One optional mechanism for removing bubbles is an air trap. For instance, a larger piece of tubing or a small chamber where air can rise out of the flow line is used. Optionally, this line is bled off to remove air bubbles built up over time. In a second instance, the interior surface of the delivery means 107 is coated with a material that repels the coupling fluid. For example, a hydrophilic coating is placed on the interior of tubing. The hydrophilic coating repels fluorocarbons. Therefore, the fluorocarbon fluid sticks together instead of forming bubbles when the fluid is advanced or withdrawn through the tubing. Similarly, a hydrophobic surface is preferably used when moving a hydrophilic fluid, such as water.

EXAMPLE VI

In a sixth example, an optional magneto-mechanical apparatus with a magnetic field modifier that, when inserted into or removed from the magnetic field between two magnet components of the apparatus, triggers a displacement of at least one of the magnet components, which is coupled to a drive or a switch. The drive 102 is used to move coupling fluid from a reservoir 101 through delivery means or channels 107 to the sample 14. The apparatus is based on coupled attracting or opposing magnets in conjunction with the insertion or removal of a magnetic field modifier. In one instance, two repelling magnets are drawn together with the insertion of a magnetic field modifier. The field modifier is optionally another magnet having an opposing pole. Removal of the field modifier returns the forces to their original states. This oscillating motion allows drive with a low energy and/or small power supply. The resulting motion of the opposing magnets is used to drive a mechanical system such as a linear, gear, ratchet, or reciprocating drive.

EXAMPLE VII

A seventh example of an automated coupling fluid delivery system is software driving a solenoid with a direct current power supply assisted by a coiled spring. The solenoid drives a gear on a threaded plunger. The plunger forces fluid out of a syringe into tubing that is directed in proximity to a source filament where it is heated prior to delivery via tubing to a sample site.

EXAMPLE VIII

In an eighth example, potential energy is used as a power supply for driving coupling fluid to a sample site 14. Power 104 used to drive the coupling fluid is, optionally, assisted by a potential energy 105 power supply. The potential energy power supply pushes on the driving means 102.

Thermal Control

In the case of a noninvasive measurement that uses an optic that contacts the sample site 14 skin during the measurement of the sample there is a potential for thermal variations due to conductive heat transfer between the skin and the contacting optic. Examples of optics in contact with the skin sample site include the tip of one or more fiber optics, a lens, or an optical window. Since conductive heat transfer is often very rapid and the effect of temperature on some near-infrared spectral features is large, the impact on the resulting spectrum is severe in some cases. For example, water that has large near-infrared absorbance bands is sensitive to temperature in both absorbance magnitude and wavelength of absorbance. Another example is near-infrared absorbances that relate to hydrogen bonding, which are known to be temperature sensitive. An exemplary noninvasive glucose concentration estimation case is when an optic at environmental ambient temperature is brought into direct contact with the skin surface, which is often at a much higher temperature than ambient temperature. In this case, a resulting sample spectrum has variation due to temperature variation due to heat transfer from the skin to the optic. In another case, heat is transferred from the optic to the skin, which also results in sample site temperature variation, which manifests in noninvasive spectra. Often the temperature variation manifested in the spectrum degrades subsequent analytical performance based upon use the spectrum.

Temperature control of the skin contacting optic to a target temperature, such as the temperature of skin, minimizes thermal deviations in the measurement of the resulting spectrum. Optional temperature control is preferably performed on one or more of a sample probe tip, sample, reference material, and coupling fluid. For example, just the tip of a sample probe temperature is controlled to about skin surface temperature. In a second example, coupling fluid is preheated to a target temperature, such as about 85, 87, 89, 91, 93, 95, or 97 degrees Fahrenheit. In a third example, a two-stage system is used that uses one mechanism to control the skin temperature and another to control the optic to the targeted skin temperature. In a fourth example, a coupling fluid is thermally controlled and the warmed coupling fluid is applied to the sample site. This prevents a thermally cool coupling fluid site from locally cooling the sample site upon application of the fluid to the sample site. In a fifth example, an active heater 108 with feedback control is used to control the optic to a target temperature and/or to control the temperature of a coupling fluid to the target temperature. In a sixth example, a thermal stability fluid and/or a coupling fluid is used to control both the skin and the optic temperature. The temperature control point is ideally set closer to the skin temperature, as opposed to the ambient temperature, as the tissue sample typically has a much greater thermal mass compared with the contacting optic. A further example of a target temperate is ninety degrees Fahrenheit plus or minus two to three degrees Fahrenheit, which represents a natural physiological mean skin temperature in a targeted ambient measurement range of 63 to 82° F. An example of implementation is to first adjust the skin to a target temperature with a coupling fluid or first stage heater and second to control an interfacing optic to the target temperature. Subsequently, the optic is brought into contact with the sample. Optionally, the reference temperature is controlled to the temperature of the sample. This allows for a background that is representative of the thermal environment of the sample.

An optional temperature control 108 device is used. A number of elements are optionally used for thermal control including auxiliary heating elements. Examples include a heat source, such as a filament, a heating strip, and a thermoelectric heater. Optionally, an internal heating element, such as an analyzer source, is used to provide heat to an optic, coupling fluid, and/or a target tissue site. For example, the high temperature source of the analyzer heats passing coupling fluid in a passive manner through heat transfer. The fluid in turn is used to cool the apparatus. For example, U.S. patent application Ser. No. 10/472,856, teaches a sample module that optionally contains a source. The source heats the module. The outer surface of the module is preferably kept cool so that it is readily handled. Coupling fluid directed near or around the source helps to cool the sampling module at the same time that the coupling fluid is brought to a thermal state that is compatible with sampling requirements. Coupling fluid is delivered from the reservoir to an input. The fluid is forced about a high temperature filament to an exit. The fluid is delivered to an interface between a sampling module and the skin tissue.

Combinations and permutations of the coupling fluid delivery methods described herein are also usable without diverting from the scope of the invention.

While the invention is described in terms of noninvasive glucose concentration estimation, the methods and apparatus described herein also apply to estimation of additional blood tissue analytes.

Those skilled in the art will recognize that the present invention may be manifested in a variety of forms other than the specific embodiments described and contemplated herein. Departures in form and detail may be made without departing from the spirit and scope of the present invention. Accordingly, the invention should only be limited by the Claims included below.

The invention claimed is:

1. A sample probe configured to communicate with a noninvasive spectroscopic analyzer to determine an analyte property from a sample site of a body part, said sample probe comprising a sample probe tip having a microfluidic fluid delivery channel in a surface of said sample probe tip, said microfluidic fluid delivery channel forming a pathway for dispersion of a coupling fluid across the surface of said sample probe tip,
wherein said microfluidic fluid delivery channel comprises a first moat circumferentially surrounding an optic in said sample probe.

2. The sample probe of claim 1, further comprising a fluid delivery aperture in said sample probe tip and proximate to said first moat, wherein said coupling fluid is delivered from a reservoir via said fluid delivery aperture to said first moat.

3. The sample probe of claim 2, further comprising a second moat in the surface of said sample probe tip, said second moat circumferentially surrounding said first moat.

4. The sample probe of claim 2, further comprising means for maintaining temperature of said coupling fluid at about ninety to ninety-two degrees Fahrenheit prior to delivery of said coupling fluid.

5. The sample probe of claim 1, further comprising means for creating a negative pressure in said first moat during use of said analyzer.

6. The sample probe of claim 1, wherein said microfluidic fluid delivery channel further comprises at least one radially extending channel.

7. The sample probe of claim 1, wherein said microfluidic fluid delivery channel further comprises said first moat coupled to at least one radially extending channel.

8. The sample probe of claim 2, further comprising means for delivering said coupling fluid from said reservoir, via said fluid delivery aperature, to said microfluidic fluid delivery channel.

9. The sample probe of claim 8, in combination with said analyzer, wherein said analyzer comprises a processor configured to control said means for delivering.

10. The sample probe of claim 9, wherein said processor is configured to operate in accordance with a control signal from a sensor.

11. The sample probe of claim 10, wherein said sensor comprises any of:
an electrical contact sensor configured to sense proximate contact of said sample probe tip with the sample site, wherein upon proximate contact of said sample probe tip with the sample site, an electrical circuit is completed and said electrical contact sensor generates a signal indicative of completion of said electrical circuit; and
a pressure sensor configured to sense proximate contact of said sample probe tip with the sample site, wherein said pressure sensor comprises a film layer with air voids internally contained, wherein said pressure sensor is configured to generate a charge and corresponding voltage indicative of different capacitive charges measured as pressure is applied to said film layer.

12. The sample probe of claim 1, in combination with said analyzer, wherein said analyzer comprises a processor configured to control positioning of said sample probe tip relative to the sample site.

13. The sample probe of claim 12, wherein said processor is configured to operate in accordance with a control signal from a sensor.

14. The sample probe of claim 13, wherein said sensor comprises any of:
 an electrical contact sensor configured to sense proximate contact of said sample probe tip with the sample site, wherein upon proximate contact of said sample probe tip with the sample site, an electrical circuit is completed and said electrical contact sensor generates a signal indicative of completion of said electrical circuit;
 a pressure sensor configured to sense proximate contact of said sample probe tip with the sample site, wherein said pressure sensor comprises a film layer with air voids internally contained, wherein said pressure sensor is configured to generate a charge and corresponding voltage indicative of different capacitive charges measured as pressure is applied to said film layer; and
 an optical sensor configured to sense proximate contact of said sample probe tip with the sample site using spectral responses from said analyzer at about 1450 nm or at about 1900 nm.

15. The sample probe of claim 1, wherein said analyte property comprises a glucose concentration, and said coupling fluid exhibits a viscosity of less than about 2.2 centistokes.

16. The sample probe of claim 1, wherein said analyte property comprises a glucose concentration, and said coupling fluid exhibits a refractive index of less than about 1.31.

17. The sample probe of claim 4, wherein said means for maintaining temperature comprises a heater.

18. The sample probe of claim 5, wherein said means for creating a negative pressure comprises a vacuum pump.

19. The sample probe of claim 8, wherein said means for delivering comprises a channel.

20. The sample probe of claim 8, wherein said means for delivering comprises a plurality of channels.

21. The sample probe of claim 8, wherein said means for delivering is integrated with said analyzer.

22. The sample probe of claim 8, wherein said means for delivering is removably operably coupled to said analyzer.

23. A method of delivering fluid to a sample site of a body part, the method comprising delivering a coupling fluid through a sample probe to a surface of a sample probe tip of said sample probe, the surface of said sample probe tip having a microfluidic fluid delivery channel forming a first pathway for dispersion of said coupling fluid across the surface of said sample probe tip,
 wherein said sample probe is configured to communicate with a non-invasive spectroscopic analyzer to determine an analyte property from the sample site, and
 wherein said microfluidic fluid delivery channel comprises a first moat circumferentially surrounding an optic in said sample probe.

24. The method of claim 23, further comprising delivering said coupling fluid from a reservoir to said first moat via a fluid delivery aperture in said sample probe tip, wherein said fluid delivery aperture is proximate to said first moat.

25. The method of claim 24, wherein the surface of said sample probe tip further has a second moat circumferentially surrounding said first moat, said second moat forming a second pathway for dispersion of said coupling fluid across the surface of said sample probe tip.

26. The sample probe of claim 23, wherein said microfluidic fluid delivery channel further comprises at least one radially extending channel.

27. The sample probe of claim 23, wherein said microfluidic fluid delivery channel further comprises said first moat coupled to at least one radially extending channel.

* * * * *

UNITED STATES PATENT AND TRADEMARK OFFICE
CERTIFICATE OF CORRECTION

| | | |
|---|---|---|
| PATENT NO. | : 8,504,128 B2 | |
| APPLICATION NO. | : 12/109224 | |
| DATED | : August 6, 2013 | |
| INVENTOR(S) | : Blank et al. | |

It is certified that error appears in the above-identified patent and that said Letters Patent is hereby corrected as shown below:

On the Title Page

In column 2 (page 3, item 56) at line 15, Under Other Publications, Change "Disseration," to --Dissertation,--.

In column 2 (page 3, item 56) at line 22, Under Other Publications, Change "Scinece" to --Science--.

In the Specification

In column 1 at line 27, Change "May." to --May--.

In column 1 at line 31, Change "May." to --May--.

In column 2 at line 42, Change "bioimpedence" to --bioimpedance--.

In column 17 at line 66, Change "historesis" to --hysteresis--.

In column 18 at line 19, Change "tissue-compression;" to --tissue compression;--.

In the Claims

In column 24 at line 37 (approx.), in Claim 8, Change "aperature," to --aperture,--.

Signed and Sealed this
Third Day of June, 2014

Michelle K. Lee
*Deputy Director of the United States Patent and Trademark Office*